United States Patent
Aydinoglu et al.

(10) Patent No.: US 11,975,082 B2
(45) Date of Patent: May 7, 2024

(54) PRODUCTION OF ANTIBACTERIAL AND REGENERATIVE DENTAL COMPOSITE USING SUPPORTIVE PHASES (FILLERS) ANTIBACTERIAL AND BIOACTIVE PROPERTIES OF WHICH ARE IMPROVED

(71) Applicant: Yildiz Teknik Universitesi, Istanbul (TR)

(72) Inventors: Aysu Aydinoglu, Ankara (TR); Afife Binnaz Hazaryoruc, Esenler/Istanbul (TR)

(73) Assignee: AVRUPA IMPLANT SANAYI VE DIS TICARET LIMITED SIRKETI, Istanbul (TR)

( * ) Notice: Subject to any disclaimer, the term of this patent is extended or adjusted under 35 U.S.C. 154(b) by 629 days.

(21) Appl. No.: 16/957,590

(22) PCT Filed: Dec. 28, 2018

(86) PCT No.: PCT/TR2018/050925
§ 371 (c)(1),
(2) Date: Jun. 24, 2020

(87) PCT Pub. No.: WO2019/132849
PCT Pub. Date: Jul. 4, 2019

(65) Prior Publication Data
US 2020/0330332 A1    Oct. 22, 2020

(30) Foreign Application Priority Data

Dec. 29, 2017 (TR) ................................ 2017/23110
Dec. 13, 2018 (TR) ................................ 2018/19265

(51) Int. Cl.
| | |
|---|---|
| *A61K 6/887* | (2020.01) |
| *A61K 6/20* | (2020.01) |
| *A61K 6/30* | (2020.01) |
| *A61K 6/62* | (2020.01) |
| *A61K 6/75* | (2020.01) |
| *A61K 6/76* | (2020.01) |
| *C08L 33/08* | (2006.01) |

(52) U.S. Cl.
CPC .............. *A61K 6/887* (2020.01); *A61K 6/20* (2020.01); *A61K 6/30* (2020.01); *A61K 6/62* (2020.01); *A61K 6/75* (2020.01); *A61K 6/76* (2020.01); *C08L 33/08* (2013.01)

(58) Field of Classification Search
CPC combination set(s) only.
See application file for complete search history.

(56) References Cited

U.S. PATENT DOCUMENTS

| | | | | |
|---|---|---|---|---|
| 4,259,075 A * | 3/1981 | Yamauchi | ............... | C07F 9/091 558/182 |
| 4,499,251 A * | 2/1985 | Omura | ................... | A61L 27/16 526/278 |
| 4,539,382 A * | 9/1985 | Omura | ................... | C07F 9/091 106/35 |
| 4,642,126 A * | 2/1987 | Zador | ...................... | C09D 4/06 427/520 |
| 4,652,274 A * | 3/1987 | Boettcher | ............... | B24D 3/30 51/293 |
| 4,871,786 A * | 10/1989 | Aasen | ....................... | C08F 4/14 523/120 |
| 5,530,038 A * | 6/1996 | Yamamoto | ................ | C09J 4/00 526/318.42 |
| 5,545,676 A * | 8/1996 | Palazzotto | ............. | A61K 6/887 522/15 |
| 6,387,981 B1 * | 5/2002 | Zhang | ..................... | A61K 6/20 524/789 |
| 6,458,868 B1 * | 10/2002 | Okada | ....................... | C07F 9/12 526/276 |
| 2003/0166737 A1 * | 9/2003 | Dede | ...................... | A61K 6/891 522/7 |
| 2005/0252413 A1 * | 11/2005 | Kangas | .................... | A61K 6/30 106/35 |
| 2005/0252414 A1 * | 11/2005 | Craig | ...................... | A61K 6/30 106/35 |
| 2005/0252415 A1 * | 11/2005 | Budd | ..................... | A61K 6/891 106/35 |
| 2005/0256223 A1 * | 11/2005 | Kolb | ....................... | A61K 6/30 523/116 |
| 2007/0123604 A1 * | 5/2007 | Xu | ......................... | A61K 6/887 524/415 |

OTHER PUBLICATIONS

16957590 Calculations (Year: 2023).*

* cited by examiner

Primary Examiner — Peter A Salamon
(74) Attorney, Agent, or Firm — Bayramoglu Law Offices LLC

(57) ABSTRACT

The present invention relates to restorative purpose acrylic dental composite filling material which are curable by light and are polymerizable, and which contains only β-tricalcium phosphate (β-TCP), nanocrystalline cellulose (NCC), hydroxy apatite particles/fibers/whiskers, Al—Sr—OF and Al—Sr—Si—OF and/or mixtures thereof as supportive phase system for conferring regenerative and antibacterial properties to composite filling materials, and relates to production method of said dental composite filling material.

8 Claims, No Drawings

PRODUCTION OF ANTIBACTERIAL AND
REGENERATIVE DENTAL COMPOSITE
USING SUPPORTIVE PHASES (FILLERS)
ANTIBACTERIAL AND BIOACTIVE
PROPERTIES OF WHICH ARE IMPROVED

CROSS-REFERENCE TO RELATED APPLICATIONS

This application is a National Stage Application of PCT/TR2018/050925, filed 28 Dec. 2018, which claims the benefit of Turkish Patent Application No. 2017/23110, filed 29 Dec. 2017, and claims the benefit of Turkish Patent Application No. 2018/19265, filed 13 Dec. 2018, and which applications are incorporated herein by reference. To the extent appropriate, a claim of priority is made to each of the above-disclosed applications.

TECHNICAL FIELD

The present invention relates to restorative purpose acrylic dental composite filling which are curable by light and are polymerizable, and relates to production of said dental composites. Dental composites mainly consist of a supportive phase comprised of ceramic based materials and a polymer based organic resin. They may also comprise several structures called as binding agent in a composite material beside the supportive phase structures and enabling the improvability of lifetime and mechanical, chemical and physical properties of the composite material by ensuring chemical binding between supportive phase and organic phase.

By means of the invention, regenerative and antimicrobial effect is achieved by using hydroxyapatite ceramics produced by biomimetic method in the composite filling structure. Furthermore by means of the invention, antimicrobial effect is achieved by using methoxyfluoride compounds such as Al—Sr—OF and Al—Sr—Si—OF at submicron dimension in the composite structure without implementing melting technique.

STATE OF THE ART

Resin-based composite (RBC) materials were first reported by Bowen in 1958. However, commercial use of resin-based composites was allowed after the author obtained the patent titled "a vinyl-silane treated fused silica and binder" in 1962. Growing of chemically cured RBCs into a concept was realized only after it was introduced to dental market in 1970. On the other hand, these materials were majorly preferred in 1st Class and 2nd Class restorations although applications conducted without using abrader in extensive restorations are limited.

Granting of patent titled "a method of repairing teeth using a composition which was curable by visible light" by Dart in 1974 and development of "total-etch" adhesives in 1980s led up RBCs cured by light by supporting clinical use with 1st Class and 2nd Class restorations [1].

Depending on increasing expectations from aesthetic dentistry recently, it has become unavoidable from developing resin composites having advanced physical and mechanic features, providing aesthetic requirement and having a clinically long lifetime with the aim of use with direct restorations. One of the most significant improvements we encounter in this field is that Nano structured particles are combined with Nano-crystals and they are used in the structure of conventional resins [2].

The history of existing resin monomers is based on a discovery of a new acid called as "acrylic acid" by a German Chemist named J. Redtenbacher. As of 1900s, methyl methacrylate polymers are also started to be produced by means of polymerization technique as well as synthesizing methacrylate and numerous ester derivatives. By the end of 1930s, poly-methyl methacrylate was first used in dentistry as denture base resins and a few years later it secured its usage as indirect filling materials. During the Second World War, after discovering benzoyl peroxide-tertiary amine redox initiator-accelerator systems in Germany, polymerization of methyl methacrylate at room temperature could be realized and thus use of these polymeric structures as direct filling materials could be provided. Whereas, these materials failed to provide required clinical expectation [3].

American dentist R. L. Bowen observing insufficient properties of methyl methacrylate resins has developed other synthetic resins with the purpose of using in dental filling materials. He has carried out studies on epoxy resins polymerizable at room temperature within this scope. Albeit epoxy resins exhibited good aesthetic features inside oral cavity, having a slow hardening stage prevented it from being used as direct filling materials [4].

Depending on the problems encountered with epoxy resins, Bowen carried out studies on a novel monomer system 2,2-bis[4-(2-hydroxy-3-methacryloxypropxy)phenyl]propan-BisGMA structure in 1956. It has been determined that this monomer system has relatively high performances compared to methyl methacrylate systems due to its high molecule weight, chemical structure, its low volatility, its low polymerization shrinkage and fast hardening features [4].

BisGMA has been widely used in commercial dental resin composites. However, color stability of monomer is insufficient, it is quite viscous, and it cannot be purified by methods such as distillation and crystallization In order to eliminate said problem, Bowen has carried out studies on liquid isomeric crystalline dimethacrylates which is a novel monomer system and exhibits eutectic formations at room temperature. Within this scope, three aromatic diesters of phthalic (P), isophthalic (I) and terephthalic (T) acids synthesized bis(2-methacryloxyethyl)-P/I/T ester monomer and purified it by recrystallization method. It has been determined that the mechanical properties of composites produced from these monomers equal to BisGMA and that the values of polymerization shrinkage fulfilled the desired characteristic. However, these monomer systems were not able to provide desired color stability under in vivo conditions [5].

Depending on their polar structures dimethacrylate resins have a tendency to adsorb water in mouth environment and exhibit hygroscopic expanding. Although that expanding has some advantages, it causes in long term to various disadvantages as decreasing of mechanic strength and corrosion resistance. Therefore, in order to minimize water holding capacity of resin, hydrophobic monomer systems obtained by removing hydroxyl groups located in BisGMA chains are developed. However, these systems could not fulfill desired mechanical properties as well [3].

Since the hydrophobic monomers could not fulfil the desired properties, several studies were carried out to improve polymers comprising fluorocarbon having characteristic of low surface energy and high hydrophobic. Within this scope, the systems of polyfluoro mono-methacrylate and octofluoropentyl methacrylate monomer are used in resin composites. Although these composite structures fulfilled the expected hydrophobic property, they were not able to provide sufficient physical and mechanical characteristics beside exhibiting particularly high polymerization shrinkage [3].

Urethane dimethacrylates (UDM) which is another monomer system used in composite resins were first synthesized from hydroxy-alkyl methacrylates and diisocyanates. This monomer has lower viscosity value while having similar molecule weight to BisGMA. Since the percentage monomer conversion of composite systems produced by using UDM monomers are higher compared to BisGMA systems, biocompatibility is also higher. These systems, also depending on their economic costs, are used as an alternative to BisGMA monomers in commercial resin composites [3, 6].

Polymerization shrinkage is the most common problem encountered on composite resins. Volume shrinkage of BisGMA based polymers is approximately around %5 and this value can be lowered by increasing loading amount of supportive phase systems [7]. Since the polymerization shrinkage is an essential parameters affecting usage period of the composite, several studies were conducted on double ring compounds exhibiting no shrinkage and polymerized by the technique of ring opening polymerization. Bailey has indicated that various double ring monomers comprising spiro ortho-esters, spiro orthocarbonates, bicyclo keto lactones and trioxabicyclo octanes, and unsaturated diketals exhibit double ring opening polymerization without showing shrinkage and/or expansion. However, it has been determined that relatively much amount of monomer not participating in polymeric structure remained in the environment at the end of reaction [3].

Developments on organic resin structure were followed by production of composites known as "compomers" and modified with poly-acids in 1994. Those composite substances are obtained by embedding the supportive phase systems like calcium-aluminum-fluorosilicate glasses into polymer resin. Compomers are dental materials which combine aesthetic properties of conventional composites and fluoride emission and adhesion properties of glass-ionomer cements. Whereas, compomers are differentiated from glass-ionomer cement in two ways: firstly glass particles are partly silanized in order to ensure binding with the resin and secondly, polymeric structure is generated as result of radical polymerization reactions following the activation of monomers by light [8].

In 1984, organic-inorganic polymeric hybrid structures called as "ormosils (organically modified silicates)" primarily and then called as "ormocers (organically modified ceramics)" by Schmidt are synthesized. In ormocers, organic and inorganic compounds are combined in nanoscopic, i.e. in molecular scale. Thereby, these substances have the characteristics of organic and inorganic components found in their structures, wherein they exhibit unique features ground of which cannot be understood yet [9]. Dentistry usage of ormocers started in year 1998 and particularly in recent years, ormocers have gained a place commercially in restorative material applications.

Utilization of silorane based organic resin monomers is one of the recent technological developments in dental commercial materials. The monomer silorane is called after siloxane and oxirane constituting its structure. In order to obtain composite materials which are suggested to be alternative to methacrylate based monomers and by which mechanical strength is maintained as well as polymerization shrinkage is decreased, silorane monomers developed within 3M ESPE have gained a commercial application field in a short time depending on the fact that they meet the desired clinical expectations [10].

In addition to decreasing polymerization shrinkage, another feature desired to be added to monomer systems is antibacterial effect. Within this scope, monomers exhibiting antibacterial features are produced instead of adding compounds releasing fluoride into the structure. Within this framework, the most promising monomer is methacrylyl-dodecylpyridinium bromide (MDPB) produced by the reaction of antibacterial agent dodecylpyridinium bromide and methacrylyl group. It has been determined in several studies that composite systems produced as result of copolymerization of conventional dental monomers and methacrylyl-dodecylpyridinium (MDP) have an effect inhibiting bacterial growth on its surface. However, in composite systems currently produced commercially, antibacterial effect is provided via supportive phase particles releasing fluoride instead of providing by that type of monomer systems [11, 12].

Three basic constituents as monomer, silane treated supportive phase and initiator are used in the first composite resin structure in 1960s. The supportive phase used by Bowen in 1963 consists of ground quartz particles which have average sizes in the range of 8-12 μm (8000-12000 nm). Depending on restrictions of macrophyll composite in aesthetic restorations (such as problems with surface polishing), miniphyll composites have been developed in 1970s. Supportive phase systems produced by pyrogenic methods have increased the polishing capability by enabling loading to composites at a maximum rate of 55%, whereas they have significantly decreased the mechanical strength [2].

Testing of supportive phase systems as mixtures was only possible in 1980s and 1990s. Restorative materials having particle size of 600-2.000 nm and comprising those hybrid supportive phase systems were commercialized as hybrid, micro-hybrid and intensified (whisker structure) composites. Even though its mechanical strength could significantly be increased along with those products, its polishability property was still in a limited degree. Maximum loading rate in those products reached to values of 70-77% by weight. Nevertheless, particle size values of conventional composites could not comply sufficiently with hydroxyapatite crystals, dentine tubules and enamel rods contained in natural structure of tooth. Therefore, potential of providing required retention between macroscopic material and nanoscopic (1-10 nm) tooth structure could not be achieved [13].

Since production of supportive phase smaller than 100 nm by grinding method is not possible, employing nanotech methods in production of supportive phase has been an innovative technique in this field by providing properties such as controlled crystal growth, homogenous final product in terms of structure and dimension. At the beginning of current century, Filtek Supreme (3MESPE, St. Paul, USA) has been commercially a milestone for nanotech applications in operative dentistry. Composite resin produced in this context comprises aggregated zirconia/silica groups which has base particle size of 5-20 nm and has proportion of 78.5% by weight, and silica based supportive phase systems having no aggregation and having a particle size of 20 nm [2].

Recently, composite systems containing composites of micro-hybrid and nanophyll together are commercialized. That novel composition has enabled that the loading proportions of supportive phase systems can be risen up to 87% by weight depending on formation of filler gaps of supportive phase content between larger particles and smaller particles [2].

Furthermore, curing techniques used for polymerization of composites have been improved in time depending on the improvement of supportive phase and monomer systems. As already mentioned above, the first composite filling materials used in the field of dentistry were polymerized with redox reactions at room temperature. Polymerization reactions of those products packed as two different material started by mixing of the products and required a long time period like 8 minutes for proper completion of the polymerization [14].

Depending on the time duration of polymerization, composite systems (Nuva; Dentsplay/Caulk) which could be photo-polymerized were developed in the later 1970s. This type of polymerization method provided the dentist with advantage of rapid curing after placing the product and capability of realizing desired contour. Primarily in those systems, quartz lamp having wavelength of 354 nm are used as UV light source, polymerization reaction proceeds over free radical formation. Although that system was advantageous at the beginning, in the next periods, several problems such as incomplete polymerization and very fast depletion of light source were encountered in cases where application is made at large amounts. Therefore, in the next periods, visible light energy was started to be applied in the range of 400-500 nm wavelength instead of UV light for photo-polymerization [15]. Firstly quartz-tungsten-halogen light sources were used in visible light systems. The most used photoinitiator in those systems is camphor-quinone [14]. Polymerization time of a restoration with a thickness of 2 mm lasts approximately 40-60 seconds by conventional quartz-tungsten-halogen light sources. Although these systems are more advantageous for polymerization compared to self-cure systems, searching of new methods is continued while energy of the light is more intensive on composite surface compared to lower areas and the light is penetrated to lower areas at lower intensity [16].

Along with the development of laser technology providing high light intensity in the range of energy band required for photo-polymerization in dental materials, dentistry applications are also developed. "Argon laser" providing 448 nm wavelength high energy output brings along various advantages such as fast polymerization in commercial dental restorative materials [17].

Another system developed for shortening the polymerization time is "Plasma Arc Unites". Short arc systems provided by use of xenon light source in this context are called as plasma arc light source. This unite consists of spark generated by applying high energy potential between two tungsten electrode and liquid gas systems. The system work at 400-500 nm wavelength and the polymerization is performed shorter than 1 second. However, some researchers suggest that the final product cannot have desired property qualification depending on completion of polymerization in such a short time [18].

Producers have developed the present system by providing "high energy" output and short application time similarly to plasma arc systems in order to keep quartz-tungsten-halogen lamp in the market. On the contrary, concerns about polymerization shrinkage have arisen depending on developing of rapid curing conditions [18].

Improvements observed on light emitting diode (LED) technology made it unavoidable to use these light sources in dentistry industry. Emitting range of blue LED light sources correspond to wavelength range of photoinitiator systems. Main advantages of said light source can be specified as follows; transportable, requiring minimum maintenance, long lifetime and emitting only at wavelength required for activation of photoinitiator [14].

Another curing method particularly used in cement technology is dual-cure method. In chemical curing method, since extra initiator left in the environment is required to be removed from the environment and long-time of waiting is required until the product is completely fitted, those problems are tried to be solved by the method of light curing. Whereas, in curing by light, a complete polymerization cannot be ensured depending on the fact that the light cannot be intensive enough in deeper points. In order to overcome those problems, dual-cure resin cement systems are developed by using both chemical and photoinitiator systems inside the products [19-21].

One of most essential points in composite restorations is conversion percentage of monomer. One of the simplest methods is applying heat performed to ensure polymerization. Heat ensures that free radicals are better diffused to monomer by reducing monomer viscosity and thereby higher monomer conversion percentage is observed. "Post cure heating" method is developed for composite systems with photoinitiator on the basis of that principle. In this method, photo-polymerization is performed by curing the composite first by conventional light source and then heat is applied [22]. This method is preferred in glass ionomer systems rather than composite filling materials.

Resin based composite restorations started with methyl methacrylate resin compositions have come a quite long way until today in terms of organic resin, inorganic phase and curing techniques. However, resin based composite filling materials do not have a structure that can imitate natural tooth structure and sufficient properties fulfilling required expectation. Therefore, considering the clinical expectation, researches for the improvement of properties of composite filling materials are continued in an increasing speed.

In 2014, Martin et al. [23] carried out studies on synthesis of a urethane multimethacrylate based monomer system which could be an alternative to BisGMA based composites causing problems such as low monomer conversion and high volume shrinkage. In this context, they produced urethane-multimethacrylate monomer by using methacryloyloxypropylphenylmethane (BMPM) and urethane-methacryloyloxyethyl (UME) starting monomers. They detected that the composite they produced exhibited lower polymerization shrinkage and higher bend strength compared to conventional composites and physical chemical and mechanical properties of the composite had a specific stability, by loading silicate supportive phase particles into the monomer system.

Liu et al. [24] pointed out the problems for homogenous mixing of Ag nanocrystals, which are used in dental composites to prevent secondary decay formation, inside the organic resin and loaded the silver particles to composite systems by modifying with organic agents. Within this scope, they examined mechanical and antibacterial properties of dental resin composites by covering Ag nanoparticles by oleic acid. They determined that modified silver nanoparticles significantly improved mechanical and antibacterial properties, such as bend strength, elasticity module, compressive strength, of the composite compared to non-modified particles.

He et al. [25] carried out studies on synthesis of antibacterial and radio-opaque dimethacrylate monomers for use with dental resin composites. Within this scope, they synthesized tertiary ammonium dimethacrylate compounds such as N,N-bis[2-(3-(methacryloxyloxy) propanamido) ethyl]-N-methyldodecyl ammonium iodide (QADMAI-12), N,N-bis[2-(3-(methacryloxyloxy)propanamido)ethyl]-N-methylhexadecyl-ammonium iodide (QADMAI-16) and N,N-bis[2-(3-(methacryloxyloxy)propanamido)ethyl]-N-methyloctadyl ammonium iodide (QADMAI-18). They also determined that monomer conversion percentages of produced composite were better compared to conventional composites in addition to antibacterial and radio-opacity properties. However, they observed that values of bend strength and elasticity module of the composites were lower compared to conventional composites.

Liu et al. [26] carried out studies on bioactive dental resin composite which is curable by light. They loaded supportive phase system which they produced by combining Poly (BisGMA)-graft-silanized whisker hydroxyapatite (PGSHW) and silanized-silica (s-$SiO_2$) nanoparticles into bisphenol-A glycidyl methacrylate (BisGMA)/triethylene glycol dimethacrylate (TEGDMA) based dental resin. They determined that the composites, which they produced, comprising PGSHW/s-$SiO_2$ hybrid supportive phase system significantly enhanced mechanical properties and monomer conversion percentage values, such as bend strength, elasticity module, compressive strength and toughness, of the substance compared to composites comprising hydroxyapatite nanoparticles. Furthermore they showed that the composite produced by in vitro bioactivity tests was capable of creating apatite.

Wu et al. [27] developed a composite which comprises dimethylaminohexadodecyl methacrylate (DMAHDM) for providing antibacterial function, and comprises Nano sized amorphous calcium phosphate (NACP) for remineralization, and which provides self-repair with the aim of finding solution to the problems such as crack and secondary decay formation occurred in composite restorations. They stated that the composite structure produced as result of their works for the first time in the literature has the abilities of crack repairing, antibacterial effect and remineralization all together after crack formation.

Chan et al. [28] carried out studies on composite systems exhibiting antimicrobial effect similarly with Wu et al. [27]. They loaded Nano sized amorphous calcium phosphate ceramics and dimethylaminododecyl methacrylate (DMADDM) monomeric structures into organic resin systems of conventional composites. They suggested as result of their works that use of those substances in composites as supportive phase systems could be appropriate by determining that Ca and P ion emission was increased in accordance with pH decreased as result of bacterial growth and that DMADDM monomer inhibited bacterial growth by exhibiting antimicrobial effect.

Zhang et. al [29], likewise Chan et al. [28], utilized silver Nanoparticles (NAg) also as supportive phase system beside dimethylaminododecyl methacrylate (DMADDM), amorphous calcium phosphate nanoparticles having antimicrobial effect and determined that the antimicrobial effect was longer compared to other composites.

Zhou et al. [30] developed a novel antimicrobial monomer system and loaded amorphous calcium phosphate nanoparticles in that system in order to prevent biofilm formation observed on composite structure and to avoid accordingly formed secondary decays. They synthesized dimethylaminododecyl methacrylate (DMADDM) monomers containing 12 carbon chains likewise the studies of Chan [28] and Zhang [29] by using dimethylaminohexane methacrylate (DMAHM) monomers containing 6 carbon chains as antimicrobial monomers and loaded amorphous calcium phosphate nanoparticles (nACP) produced by spray dryer technique as supportive phase into that structure. They determined that DMADDM monomer showed more antimicrobial effect compared to DMAHM monomer as result of their studies. They determined that DMADDM-NACP Nano composites had similar strength values compared to systems in which tertiary ammonium dimethacrylates are used, whereas they lowered biofilm formation on the composite only by 5%. In view of the findings they obtained, they suggested that the length of carbon chain of monomer was quite effective on antimicrobial activity.

Jan et al. [31], focused on polymerization shrinkage which is one of the most common problems in dental restorations and intended to reduce polymerization shrinkage and to enhance hardness values of the composite structure by modifying dimethacrylate monomers with diisocyanate side groups. As result of studies carried out, they found that polymerization shrinkage could be reduced and surface hardness of the composite could be increased depending on use of diisocyanate side groups and on the length of chain.

Khan et al. [32] carried on works for enhancing the binding between filling material and tooth interface and for providing fluoride emission. In this context, they bound Nano fluoroapatite (nFA) particles produced by sol-gel method to organic resin comprised of urethane monomeric structures via diisocyanate side chains. They determined that the produced composite exhibited a better binding to tooth structure compared to conventional composites and that fluoride emission was realized in long term and suggested that the composite structure could be used as filling material.

Liu et al. [33] examined morphological, loading and mechanical characteristics of the composites comprising BisGMA/TEGDMA organic resin structures containing and not containing silica nanoparticles by adding silanized hydroxyapatite (DK-sHA) particles having similar morphology with sea urchin to the composite. They found that mechanical properties of the composite could be enhanced by loading DK-sHA supportive phase at 5% and 10% by weight to the composite structures not containing silica and determined that although elasticity module and micro-hardness values of the composite were increased at loading levels of 20% to 30%, the strength remained as the same. They determined that DK-sHA was placed inside the resin as embedded and homogenously distributed inside the composite when compared to silanized amorphous hydroxyapatite and whisker hydroxyapatite. When loaded into composite systems in which silica particles were also present, it was determined that strength and elasticity module values of the composite could be significantly improved.

Tauböck et al. [34] examined the effect of alkali bioactive glass nanoparticles ($SiO_2$—$Na_2O$—$CaO$—$P_2O_5$—$Bi_2O_3$) loaded into the dental resin on properties of the composite. They found that loading at 20% proportion was not effective on micro-hardness whereas it significantly increased the monomer conversion percentage.

Hojati et al. [35] loaded ZnO nanoparticles into the composite material for enhancing antimicrobial effect of the dental restorative materials and evaluated the antimicrobial effect of composite on *Streptococcus mutans* bacteria and the physical and mechanical properties of the material. They determined that bacterial growth was significantly reduced by increasing ZnO nanoparticles loading and that the values of bend strength, compressive module and monomer conversion were not changed when compared to conventional composite systems.

Jan et. al [36] modified Bis-GMA monomers and added the functional side groups of toluene 2,4-diisocyanate (TDI) and 1,6-hexamethylene diisocyanate (HDI) into those monomer system in order to find solution to polymerization shrinkage problem of the dental composites. They found that the resin containing high amounts of functional side groups and modified with TDI exhibited less cytotoxic effect compared to HDI modified resin. Additionally, they suggested that TDI modified resin caused less toxic effect compared to BisGMA monomers depending on compression of toxic resin monomers inside the structure.

To sum up, when recently carried out studies on existing commercial dental composites are examined, it can be seen that the restorative filling materials provide sufficient physical and mechanical strength now. Therefore, researches on resin based composite filling materials conducted in the last three years focused intensively on enhancing chemical properties of the composite such as reducing polymerization shrinkage and increasing percentages of monomer conversion, as well as enhancing biological properties of the composite such as antimicrobial and remineralization effect.

OBJECT OF THE INVENTION

This invention includes production of composite based restorative materials suitable for clinical demands for use by conservative dental treatments. The results intended within this scope;
1. Enhancing the edge compatibility and inhibiting secondary decays by reducing polymerization shrinkage,
2. Inhibition of secondary decay formation by supportive phase systems containing fluoride
3. Enhancement of remineralization property by bioactive ceramics like hydroxyapatite,
4. Maintaining the mechanical properties while enhancing antibacterial and biological properties.

DETAILED DESCRIPTION OF THE INVENTION

1. Synthesis of Supportive Phase Systems
1.1. Biomimetic Hydroxyapatite Synthesis Firstly, "Synthetic Body Fluid (SBF)" solution is prepared for biomimetic hydroxyapatite (BHA) synthesis. The "SBF solution" prepared by Taş [60] and having a composition which is the most similar one to human plasm among the solutions of the literature is used.

Hydroxyapatite (HA) widely preferred in hard tissue applications is produced by using $Ca(NO_3)_2 \cdot 4H_2O$ or $Ca(OH)_2$ or $Ca(CH_3COO)_2$ or $CaCl_2$ as calcium source, and $(NH_4)_2HPO_4$ or $NH_4H_2PO_4$ or $K_2HPO_4$ or $H_3PO_4$ as phosphor source, at 37° C. inside the synthetic body fluid (SBF) with pH of 7.4 according to the reaction of the Equation 1. Amounts of the materials used in synthesizing of BHA ceramic powders are adjusted such that Ca/P proportion of the resulting product is between 1.5 and 1.8, for example is 1.5, 1.55, 1.6, 1.65, 1.7, 1.75, 1.8.

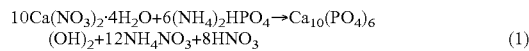

$$10Ca(NO_3)_2 \cdot 4H_2O + 6(NH_4)_2HPO_4 \rightarrow Ca_{10}(PO_4)_6(OH)_2 + 12NH_4NO_3 + 8HNO_3 \quad (1)$$

1. The first stage includes preparation of starting solutions. In this stage, 1M $Ca(NO_3)_2 \cdot 4H_2O$ and 1.2M $(NH_4)_2HPO_4$ are added respectively into 1000 ml and 500 ml SBF solution and are dissolved by using magnetic stirrer with heater at 500 rpm and 37° C.
2. PH value of $Ca(NO_3)_2 \cdot 4H_2O$ solution is adjusted to 8 by using SVS:$NH_3$ solution in proportion of 2:1.
3. Following the pH adjustment, $(NH_4)_2HPO_4$ solution is added to $Ca(NO_3)_2 \cdot 4H_2O$ solution at a speed of 3-5 ml/min and is stirred for about 1-2 hours.

4. The present mixture is aged by incubating at 37° C. for 24-48 hours and then filtered by using blue band filter paper by vacuumed filtration method.
5. Resulting white and viscous precipitation is dried at 80° C. and ground in agate mortar by being calcined for 1 hour at 900° C. in muffle furnace.
6. Resulting biomimetic hydroxyapatite ceramic powder is abbreviated as BHA.

1.2. Zirconia Synthesis

Zirconia nanoparticles can be synthesized by various methods such as sol-gel, precipitation, burning, condensation and thermal fragmentation of zirconium compounds The most common method today is sol-gel method among those methods for synthesizing of Nano ceramics as zirconia. Crystal phase, crystal size and other properties of zirconia nanoparticles are based on several parameters such as starter type, pH value of solution during hydrolyze and thermal process. In sol-gel method, various parameters such as purity, homogeneity and physical properties of zirconia ceramic can be controlled at low temperatures [61]

In the present work, zirconia ceramic is synthesized by using sol-gel technique and zirconium oxy nitrate metal salt as starting material and steps of experimental works are as follows:
1. 2.5 M $ZrO(NO_3)_2 \cdot xH_2O$, water in proportion to 400 ml 3:5 (v/v) is dissolved inside ethanol.
2. 120 ml of $HNO_3$ is added to the solution.
3. In order to prevent aggregation by forming complex with metal salt and to provide a homogenous distribution [61] PEG solution in ratio of 1% by weight is added to resulting acidic solution and sol solution is obtained by making zirconia salt be hydrolyzed.
4. The mixture is dried at 200° C. by using magnetic stirrer with heater and also dried in incubator at 150° C. for one night and thus the gel is obtained by resulting condensation reactions.
5. The dried mixture is calcined for 1 hour in muffle furnace at 1100° C.
6. Resulting zirconia ceramic powder is abbreviated as $ZrO_2$.

1.3 3% Mole Yttria Doped Tetragonal Zirconia Synthesis

It is in three different crystal form in atmospheric conditions as zirconia monoclinic (up to 1170° C.), tetragonal (between 1170-2370° C.) and cubic (between 2370-2680° C.) [64]. Zirconia being in monoclinic phase at room temperature [65] transforms into cubic and tetragonal phase at high temperatures. On the other hand, in order for those phases formed at high temperatures to be stable at room temperatures, agents such as CaO, MgO, $Y_2O_3$ and $CeO_2$ should be placed into the zirconia lattice [66]. While zirconia containing $Y_2O_3$ in the mole ratio of 8% or more is in cubic phase at room temperature, zirconia containing $Y_2O_3$ in the mole ratio of 3% is in tetragonal phase at room temperature. In loading made in the ratio between 3-8% mole, zirconia involves cubic and tetragonal phases in its structure [67]. In the present work, 3% mole yttria doped tetragonal zirconia ceramic is synthesized by using sol-gel technique likewise zirconia synthesis:
1. 1.15 M $ZrO(NO_3)_2 \cdot xH_2O$, water in proportion to 250 ml 1:5 (v/v) is dissolved inside ethanol.
2. 80 ml of $HNO_3$ is added to the solution.
3. 0.35M $Y(NO_3)_3 \cdot 6H_2O$ is added to resulting acidic solution.
4. In order to prevent aggregation by forming complex with metal salt and to provide a homogenous distribution [61] PEG solution in ratio of 1% by weight is added to resulting acidic solution and sol solution is obtained by making metal salts be hydrolyzed.

5. The mixture is dried at 200° C. by using magnetic stirrer with heater and also dried in incubator at 150° C. for one night and thus the gel is obtained by resulting condensation reactions.

6. The dried mixture is calcined for 1 hour in muffle furnace at 1100° C.

7. Resulting 3% mole yttria doped tetragonal zirconia ceramic powder is abbreviated as 3YSZ.

1.4. Silica Synthesis

Silica powders to be used as supportive phase in the present work is obtained from commercial LUDOX® HS-40; LUDOX® AM; LUDOX® AS-40; LUDOX® TM-50; LUDOX® AS-30; LUDOX® TMA; LUDOX® CL; LUDOX® SM; LUDOX® HS-30; LUDOX® TM-40; LUDOX® LS; LUDOX® CL-X colloidal silica solutions:

Method 1

1. Colloidal silica solution is dried in incubator at 80° C.
2. Dried powders are ground for one (1) day long in ball mill.
3. Ground powders are sifted through a sieve with mesh of maximum ≤250.
4. Resulting silica ceramic powder is abbreviated as $SiO_2$.

Method 2

1. Water of colloidal silica solution is evaporated in rotary evaporator at 80° C.
2. Then the silica is dried in vacuumed incubator at 80° C.
3. Dried powders are ground for one (1) day long in ball mill.
4. Ground powders are sifted through a sieve with mesh of ≤250.
5. Resulting silica ceramic powder is abbreviated as $SiO_2$.

Method 3

1. Colloidal silica solution is dried first by using freeze dryer then in vacuumed incubator at 80° C.
2. Dried powders are ground for one (1) day long in ball mill.
3. Ground powders are sifted through a sieve with mesh of ≤250.
4. Resulting silica ceramic powder is abbreviated as $SiO_2$.

1.5. Silica/Zirconia Group Synthesis

One of the most essential properties demanded by dentist and patient in dental composites in the recent years is that the composites can fulfil aesthetic expectation. At this point, dental composite structures are desired to imitate view of the natural tooth as much as possible. Silica/zirconia Nanoclusters are quite attractive supportive phase systems in fulfilling aesthetic expectation thanks to optical features they have and outstanding mechanical features they brought in dental composites [68]. Silica/zirconia Nanoclusters which are a metal oxide can be synthesized by various methods such as wet impregnation, sol-gel, chemical precipitation and sol-gel at low temperatures [69]. By means of those methods, Zr ions are arranged into silica lattice and a structure containing mixture of metal oxides is formed [70]. In the present work, silica/zirconia Nanoclusters are synthesized on the basis of wet impregnation [71] but drying and calcination process is done likewise sol-gel method without applying filtration process after sedimentation. In Si/Zr Nanocluster structure to be obtained, the ratio of Si/Zr varies between 1 and 20 depending on intended opacity value [69].

1. pH value of 500 ml colloidal silica solution is adjusted to 2.5 by diluted $HNO_3$ solution.
2. That solution is slowly added to solution of 230.65 ml zirconyl acetate and stirred for 1 hour.
3. The mixture is dried in incubator or in rotary evaporator at 80° C. and calcined in muffle furnace for 4 hours at 550° C.
4. Calcined powder is ground in ball mill for one day long and sifted through ≤450 mesh sieve.
5. Resulting silica/zirconia Nanocluster ceramic powder is abbreviated as Si/Zr Nanocluster.

1.6. Titanium Oxide

Titanium oxide is purchased commercially and used as supportive phase system without subjecting to any process.

1.7. Methoxyfluoride Synthesis

Metal-oxyfluoride systems also called as acid reactive supportive phase system are used in dental composites as fluorine emission agent. Main object of those structures used in dental composite systems arises due to preventing secondary decay formation in areas where restoration is made. Metal oxides, metallic salts and glass systems constitute acid-reactive supportive phase systems group. Floro-alumino-silicate (FAS) glasses are examples of metal-oxyfluoride systems. While these systems are prepared by melting technique, high particle dimension they have restricts their use as supportive phase system in dental composites. Metal oxides which are produced as alternative to those systems and contain a trivalent metal, oxygen, fluorine, alkali metal and preferably silicon can be used in dental composite depending on their controllable surface area values. Oxygen and fluorine atom in these structures bind to same atom. For example, aluminum binds to oxygen and fluorine aluminum in the structure in which it is present as trivalent atom and is together with $Al_2O_3$ and $AlF_3$ structures within the same lattice form. Typically preferred structure in these structure as alkali earth metal is strontium metal. Proportion of trivalent metal and alkali earth metal in oxyfluoride material influences the properties of the composite as chemical and curing efficiency. For instance, using alkali earth metal in the structure at high proportion increases reactivity of the composite and leads to emission of undesired other materials as well as fluorine [184]. In the present work, metal-oxyfluoride systems prepared by precipitation technique as alternative to FAS glasses which are used as fluorine emission agent in dental composites are used. In this context, two different fluorine emission agents as Al—Sr-oxyfluoride and Al—Sr—Si-oxyfluoride not containing silicon are produced as supportive phase system. Experimental steps are sorted as follows:

Production of Al—Sr-Oxyfluoride Supportive Phase Systems 1. 2M and 80 mL $Al(NO_3)_3 \cdot 9H_2O$ solution is mixed with 2M and 20 mL $Sr(NO_3)_2$ solution. Prepared solution is called as "cation solution".
2. 2M and 720 mL $NH_4OH$ solution is mixed with 2M and 180 mL $NH_4F$ solution and prepared solution is called as "anion solution".
3. Cation solution is added to anion solution under strong stirring and stirred for 1 hour.
4. White and viscous precipitation resulted at the end of 1 hour stirring is filtered by vacuumed filtration method and rinsed with purified water.
5. Precipitations are dried in incubator at 100° C. for one night and subsequently kept for 1 hour at 250° C.
6. Dried powders are ground in ball mill for three hours and sifted through ≤250 mesh sieve.

Production of Al—Sr—Si Oxyfluoride Supportive Phase Systems 1. 2M and 67 mL $Al(NO_3)_3 \cdot 9H_2O$ solution is mixed with 2M and 33 mL $Sr(NO_3)_2$ solution. Prepared solution is called as "cation solution".

2. 2M and 67 mL Na$_2$SiO$_3$ solution, 2M and 653 mL NH$_4$OH solution and 2M and 180 mL NH$_4$F solution are mixed with each other and prepared solution is called as "base solution".

3. Cation solution is added to base solution under strong stirring and stirred for 1 hour.

4. White and viscous precipitation resulted at the end of 1 hour stirring is filtered by vacuumed filtration method and rinsed with purified water.

5. Precipitations are dried in incubator at 100° C. for one night and subsequently kept for 1 hour at 250° C.

6. Dried powders are ground in ball mill for three hours and sifted through ≤250 mesh sieve.

Steps (method 1) of a method used in the scope of experimental works, comprising functionalization by using A174, of supportive phase systems of biomimetic hydroxyapatite (BHA), zirconia (ZrO$_2$), silica (SiO$_2$), silica/zirconia nanocluster (Si/Zr nanocluster) and commercially available titania (TiO$_2$) produced as supportive phase system in the present work are sorted as follows:

1. Suitable amount of A174 is added to 380 ml ethanol: water (1:3) in a glass bottle that is capped and pH value of the solution is adjusted to 3.5 by acetic acid solution and stirred for 30 minutes.

2. Then supportive phase system to be modified under strong stirring is added to this solution and stirred for 30 minutes in magnetic stirrer with heater and stirred for 10 minutes in ultrasonic water bath.

3. After stirring, it is treated for 3 hours at 80° C. in condenser.

4. The mixture filtered by vacuumed filtration is rinsed in ethanol/water solution for removing silanizing agent that is not reacting.

5. Finally, resulting precipitations are dried for 24 hours at 60° C. in vacuumed incubator.

Steps (method 2) of another method used in the scope of experimental works, comprising functionalization by using A174, of supportive phase systems of biomimetic hydroxyapatite (BHA), zirconia (ZrO$_2$), silica (SiO$_2$), silica/zirconia nanocluster (Si/Zr nanocluster) and commercially available titania (TiO$_2$) produced as supportive phase system in the present work are sorted as follows:

1. Suitable amount of A174 is added to 380 ml ethanol: water (1:3) located inside closed system reactor and in inert environment.

2. PH value of the solution is adjusted between 2-4 by acetic acid and stirred for 30 minutes.

3. Supportive phase system to be modified under strong stirring is added and stirred.

4. It is treated for 1-3 hours at 60-80° C. in inert gas environment under condenser. Filtered mixture is rinsed inside ethanol/water solution to remove reaction residue.

5. It is dried in clay incubator or in vacuumed incubator at 60-80° C.

The proportion between silane amount (X) to be used as binding agent and supportive phase amount to be treated was suggested and determined with the following formula [75]:

$$X = A \times f / \omega \qquad (7)$$

X: Binding agent amount (g), f: Supportive phase amount (g), A: Surface area of supportive phase (m2/g), ω: Wetting surface of silane (314 m$^2$/g)

Production of Composite Filling Materials (Method 1)

1. BisGMA (1-5%) is stirred in ultrasonic water bath for 10 minutes at 40° C. Organic resin part of the composite structure is prepared by adding HEMA (5-10%), UDMA (5-10%) and TEGDMA (1-5%) therein.

2. Only SiO$_2$, SiO$_2$/Silane, Si/Zr nanocluster, Si/Zr/Silane nanocluster, TiO$_2$, TiO$_2$/Silane, ZrO$_2$, ZrO$_2$/Silane, 3YSZ, β-tricalcium phosphate (β-TCP), nanocrystalline cellulose (NCC), hydroxyapatite particles/fibers/whiskers, Al—Sr—OF and Al—Sr—Si—OF in proportion varying between 50-90% by weight and/or supportive phase system containing the mixture of these materials are added to prepared resin mixture and stirred for one day in ultrasonic water bath or by speed mixer until a homogenous mixture is obtained.

3. Camphoquinone or diphenyl(2,4,6-trimethylbenzoyl) phosphine oxide or phenyl bis(2,4,6-trimethylbenzoyl)phosphine oxide or 1-phenyl-1,2-propanedione (0.2%) and 4-EDMAB (0.8%) is added to prepared mixture and stirred for 3 hours in ultrasonic bath.

Production of Composite Filling Materials (Method 2)

1. BisGMA (1-5%) is stirred in ultrasonic water bath for 10 minutes at 40° C. and organic part of the composite structure is prepared by adding HEMA (5-10%), UDMA (5-10%) and TEGDMA (1-5%) therein.

2. Only SiO$_2$, SiO$_2$/Silane, Si/Zr nanocluster, Si/Zr/Silane nanocluster, TiO$_2$, TiO$_2$/Silane, ZrO$_2$, ZrO$_2$/Silane, 3YSZ, β-tricalcium phosphate (β-TCP), nanocrystalline cellulose (NCC), hydroxyapatite particles/fibers/whiskers, Al—Sr—OF and Al—Sr—Si—OF in proportion varying between 50-90% by weight and/or supportive phase system containing the mixture of these materials and camphoquinone or diphenyl(2,4,6-trimethylbenzoyl)phosphine oxide or phenyl bis(2,4,6-trimethylbenzoyl)phosphine oxide or 1-phenyl-1, 2-propanedione and 4-EDMAB in proportion of 0.5-1.0% by weight is added to organic matrix mixture and stirred by speed mixer.

3. The samples are kept in vacuumed incubator for 30 minutes at 37° C. for removing air bubbles which could be present in the structure of mixture.

Compositions of the dental composites are given in the following.

Organic Resin:

TABLE 1

Organic composition of dental composites

| Constituent | Amount (% by Weight) |
| --- | --- |
| BisGMA | 1-5 |
| HEMA | 5-10 |
| UDMA | 5-10 |
| TEGDMA | 1-5 |
| CQ | 0.1-0.5 |
| Diphenyl(2,4,6-trimethylbenzoyl)phosphine oxide | 0.1-0.5 |
| phenyl bis(2,4,6-trimethylbenzoyl)phosphine oxide | 0.1-0.5 |
| 1-phenyl-1,2-propanedione | 0.1-0.5 |
| 4-EDMAB | 0.5-1.0 |

Supportive Phase:

TABLE 2

Supportive phase systems used in dental composites and their proportions by weight

| Constituent | Feature | Amount (% by Weight) |
| --- | --- | --- |
| SiO$_2$ | Main Phase | 10-90 |
| SiO$_2$/Silane | Main Phase | 10-90 |

TABLE 2-continued

Supportive phase systems used in dental composites and their proportions by weight

| Constituent | Feature | Amount (% by Weight) |
|---|---|---|
| Si/Zr nanocluster | Main Phase | 10-90 |
| Si/Zr/Silane nanocluster | Main Phase | 10-90 |
| TiO$_2$ | Opacifier and antimicrobial agent | 0.1-20 |
| TiO$_2$/Silane | Opacifier and antimicrobial agent | 0.1-20 |
| ZrO$_2$ | Opacifier | 0.1-20 |
| ZrO$_2$/Silane | Opacifier | 0.1-20 |
| 3YSZ | Opacifier | 0.1-20 |
| β-tricalcium phosphate (β-TCP) | Antimicrobial and regenerative phase | 1-40 |
| hydroxyapatite particles/fibers/whiskers | Antimicrobial and regenerative phase | 1-40 |
| nanocrystalline cellulose (NCC) | Antimicrobial phase | 1-40 |
| Al—Sr—OF | Antimicrobial phase | 1-40 |
| Al—Sr—Si—OF | Antimicrobial phase | 1-40 |

Dental composites should be in conformity with natural tooth color. In this context, pigments used in structures of dental composites are essential. These pigments should be stable in mouth environment and should not exhibit color change. Generally, oxide pigments such as iron oxide (Fe$_2$O$_3$-red) or ferric hydroxide (FeOOH-yellow) are used in dental composites [31]. In the scope of present patent application, composite products given in Table 1 can be in following color groups in accordance with Vita Classic (Vita Zahnfabrik, Bad Sackingen, Germany);

A (Yellow-red)—A1, A2, A3, A3.5
B (Yellow)—B1, B2, B3
C (Gray)—C1, C2, C3
D (Red-Gray)—D2, D3, D4.

In order to provide respective colors, Duranat Yellow Iron Oxide (Pigment Yellow 42 & 43 Cl 77492), Duranat Red Iron Oxide (Pigment Red 101 Cl 77491), Phenylbis(2,4,6-trimethylbenzoyl)phosphine oxide, 1-Phenyl-1,2-propanedione 98%, Diphenyl (2,4,6-trimethylbenzoyl) phosphine oxide, Duranat Brown Iron Oxide (Pigment Brown), Duranat Black Iron Oxide (Pigment Black 11 Cl 77499), iron oxide (Fe$_2$O$_3$-red), ferric hydroxide (FeOOH-yellow) or mixtures thereof in the proportion of 0.01-1% by weight can be used in composites.

In order to obtain opaque products in composite fillings, color pigments (E171 Titanium Dioxide; Pigment White 6 Cl 77891;) containing TiO$_2$ and/or TiO$_2$ can be used in structure.

REFERENCES

[1] I. M. Tomaszewska, J. O. Kearns, N. Ilie, G. J. P. Fleming, Journal of Dentistry.
[2] E. G. Mota, K. Subramani, Chapter 4—Nanotechnology in Operative Dentistry: A Perspective Approach of History, Mechanical Behavior, and Clinical Application, in: K. Subramani, W. Ahmed (Eds.) Emerging Nanotechnologies in Dentistry, William Andrew Publishing, Boston, 2012, pp. 49-69.
[3] A. Peutzfeldt, European Journal of Oral Sciences, 105 (1997) 97-116.
[4] R. Bowen, G. Paffenbarger, A. Mullineaux, The Journal of prosthetic dentistry, 20 (1968) 426-437.
[5] R. Bowen, Journal of dental research, 49 (1970) 810-815.
[6] C. N. Bowman, N. B. Cramer, Google Patents, 2013.
[7] M. Patel, M. Braden, K. Davy, Biomaterials, 8 (1987) 53-56.
[8] J. M. Meyer, M. A. Cattani-Lorente, V. Dupuis, Biomaterials, 19 (1998) 529-539.
[9] N. Moszner, A. Gianasmidis, S. Klapdohr, U. K. Fischer, V. Rheinberger, Dental Materials, 24 (2008) 851-856.
[10] W. Weinmann, C. Thalacker, R. Guggenberger, Dental Materials, 21 (2005) 68-74.
[11] S. Imazato, J. McCabe, Journal of dental research, 73 (1994) 1641-1645.
[12] C. Farrugia, J. Camilleri, Dental Materials.
[13] D. A. Terry, Practical procedures & aesthetic dentistry: PPAD, 16 (2004) 417-422.
[14] F. A. Rueggeberg, The Journal of Prosthetic Dentistry, 87 (2002) 364-379.
[15] E. C. Dart, J. Nemcek, Google Patents, 1978.
[16] F. A. Rueggeberg, W. F. Caughman, J. W. Curtis, Jr., Operative dentistry, 19 (1994) 26-32.
[17] G. L. Powell, R. J. Blankenau, Dental Clinics of North America, 44 (2000) 923-930.
[18] F. A. Rueggeberg, J. W. Ergle, D. J. Mettenburg, Journal of esthetic dentistry, 12 (2000) 340-349.
[19] F. A. Rueggeberg, W. F. Caughman, Operative dentistry, 18 (1993) 48-55.
[20] A. H. Darr, P. H. Jacobsen, Journal of oral rehabilitation, 22 (1995) 43-47.
[21] W. F. Caughman, D. C. Chan, F. A. Rueggeberg, J Prosthet Dent, 86 (2001) 101-106.
[22] J. W. McLean, Journal of esthetic dentistry, 6 (1994) 195-206.
[23] G. C. Martim, T. R. Detomini, I. T. A. Schuquel, E. Radovanovic, C. S. Pfeifer, E. M. Girotto, Dental Materials, 30 (2014) 155-163.
[24] F. Liu, R. Wang, Y. Shi, X. Jiang, B. Sun, M. Zhu, Progress in Natural Science: Materials International, 23 (2013) 573-578.
[25] J. He, E. Söderling, L. V. J. Lassila, P. K. Vallittu, Dental Materials, 30 (2014) 968-976.
[26] F. Liu, X. Jiang, Q. Zhang, M. Zhu, Composites Science and Technology, 101 (2014) 86-93.
[27] J. Wu, M. D. Weir, M. A. S. Melo, H. H. K. Xu, Journal of Dentistry, 43 (2015) 317-326.
[28] C. Chen, M. D. Weir, L. Cheng, N. J. Lin, S. Lin-Gibson, L. C. Chow, X. Zhou, H. H. K. Xu, Dental Materials, 30 (2014) 891-901.
[29] K. Zhang, L. Cheng, E. J. Wu, M. D. Weir, Y. Bai, H. H. K. Xu, Journal of Dentistry, 41 (2013) 504-513.
[30] C. Zhou, M. D. Weir, K. Zhang, D. Deng, L. Cheng, H. H. K. Xu, Dental Materials, 29 (2013) 859-870.
[31] Y.-D. Jan, B.-S. Lee, C.-P. Lin, W.-Y. Tseng, Journal of the Formosan Medical Association, 113 (2014) 242-248.
[32] A. S. Khan, S. Aamer, A. A. Chaudhry, F. S. L. Wong, I. U. Rehman, Materials Science and Engineering: C, 33 (2013) 3458-3464.
[33] F. Liu, B. Sun, X. Jiang, S. S. Aldeyab, Q. Zhang, M. Zhu, Dental Materials, 30 (2014) 1358-1368.
[34] T. T. Tauböck, M. Zehnder, T. Schweizer, W. J. Stark, T. Attin, D. Mohn, Dental Materials, 30 (2014) 868-875.
[35] S. Tavassoli Hojati, H. Alaghemand, F. Hamze, F. Ahmadian Babaki, R. Rajab-Nia, M. B. Rezvani, M. Kaviani, M. Atai, Dental Materials, 29 (2013) 495-505.
[36] Y.-D. Jan, B.-S. Lee, C.-P. Lin, W.-Y. Tseng, Journal of the Formosan Medical Association, 113 (2014) 349-355.
[37] H. M. Kopperud, G. F. Johnsen, S. Lamolle, I. S. Kleven, H. Wellendorf, H. J. Haugen, Dental Materials, 29 (2013) 824-834.

[38] R. Cilli, J. C. Pereira, A. Prakki, Journal of Dentistry, 40 (2012) 1144-1150.
[39] F. K. Wahab, F. J. Shaini, S. M. Morgano, The Journal of Prosthetic Dentistry, 90 (2003) 168-174.
[40] L. C. Boaro, F. Gonçalves, T. C. Guimarães, J. L. Ferracane, C. S. Pfeifer, R. R. Braga, Dental Materials, 29 (2013) 398-404.
[41] B. Pick, M. Pelka, R. Belli, R. R. Braga, U. Lohbauer, Dental Materials, 27 (2011) 664-669.
[42] H. M. Barakah, N. M. Taher, The Journal of Prosthetic Dentistry, 112 (2014) 625-631.
[43] L. C. C. Boaro, N. R. Fróes-Salgado, V. E. S. Gajewski, A. A. Bicalho, A. D. C. M. Valdivia, C. J. Soares, W. G. M. Júnior, R. R. Braga, Dental Materials, 30 (2014) 984-992.
[44] N. Ilie, R. Hickel, Dental Materials, 27 (2011) 348-355.
[45] N. Ilie, R. Hickel, Clin Oral Invest, 13 (2009) 427-438.
[46] N. Ilie, R. Hickel, A. Valceanu, K. Huth, Clin Oral Invest, 16 (2012) 489-498.
[47] S. Hahnel, S. Schultz, C. Trempler, B. Ach, G. Handel, M. Rosentritt, Journal of the Mechanical Behavior of Biomedical Materials, 4 (2011) 237-244.
[48] C. Poggio, M. Lombardini, S. Gaviati, M. Chiesa, Journal of Conservative Dentistry: JCD, 15 (2012) 237-241.
[49] R. Guggenberger, W. Weinmann, O. Kappler, J. Fundingsland, C. Thalacker, Journal of dental research, 86 (2007) 403.
[50] G. W. Marshall Jr, S. J. Marshall, J. H. Kinney, M. Balooch, Journal of Dentistry, 25 (1997) 441-458.
[51] K. Okazaki, F. Nishimura, S. Nomoto, Shika Zairyo Kikai, 8 (1989) 382-387.
[52] S. Wongkhantee, V. Patanapiradej, C. Maneenut, D. Tantbirojn, Journal of Dentistry, 34 (2006) 214-220.
[53] O. M. El Mowafy, D. C. Watts, Journal of dental research, 65 (1986) 677-681.
[54] N. Martin, N. M. Jedynakiewicz, A. C. Fisher, Dental Materials, 19 (2003) 77-86.
[55] R. R. Moraes, L. S. Gonçalves, A. C. Lancellotti, S. Consani, L. Correr-Sobrinho, M. A. Sinhoreti, Operative dentistry, 34 (2009) 551-557.
[56] T. Haenel, B. Hausnerová, J. Steinhaus, R. B. T. Price, B. Sullivan, B. Moeginger, Dental Materials, 31 (2015) 93-104.
[57] U. Lohbauer, M. Pelka, R. Belli, J. Schmitt, E. Mocker, K. D. Jandt, F. A. Müller, Operative dentistry, 35 (2010) 579-586.
[58] D. Marovic, V. Panduric, Z. Tarle, M. Ristic, K. Sariri, N. Demoli, E. Klaric, B. Jankovic, K. Prskalo, Journal of Molecular Structure, 1044 (2013) 299-302.
[59] V. Susila Anand, V. Balasubramanian, Materials Science and Engineering: B, 181 (2014) 33-38.
[60] A. Cüneyt Tas, Biomaterials, 21 (2000) 1429-1438.
[61] F. Heshmatpour, R. B. Aghakhanpour, Powder Technology, 205 (2011) 193-200.
[62] B. J. Sabacky, T. M. Spitler, Google Patents, 2006.
[63] M. Niederberger, N. Pinna, Metal Oxide Nanoparticles in Organic Solvents: Synthesis, Formation, Assembly and Application, Springer, 2009.
[64] M. Tahmasebpour, A. A. Babaluo, M. K. R. Aghjeh, Journal of the European Ceramic Society, 28 (2008) 773-778.
[65] F. Heshmatpour, R. B. Aghakhanpour, Advanced Powder Technology, 23 (2012) 80-87.
[66] F. Davar, A. Hassankhani, M. R. Loghman-Estarki, Ceramics International, 39 (2013) 2933-2941.
[67] Z. Zhang, J. Liu, F. Wang, J. Kong, X. Wang, Ceramics International, 37 (2011) 2549-2553.
[68] B. D. Craig, Google Patents, 2014.
[69] M. M. Natile, A. Galenda, A. Glisenti, S. Mascotto, S. Gross, Journal of Non-Crystalline Solids, 355 (2009) 481-487.
[70] R. G. Rodriguez Avendaño, J. A. De Los Reyes, T. Viveros, J. A. Montoya De La Fuente, Catalysis Today, 148 (2009) 12-18.
[71] S. Wang, J. Guo, X. Huang, B. Li, Materials Letters, 25 (1995) 151-155.
[72] K. L. Mittal, Silanes and Other Coupling Agents, Taylor & Francis, 2009.
[73] J.-S. Kang, C. Yu, F.-A. Zhang, Iran Polym J, 18 (2009) 927-935.
[74] M. M. Karabela, I. D. Sideridou, dental materials, 24 (2008) 1631-1639.
[75] C. Tamas, M. Moldovan, C. Prejmerean, A. Colceriu, G. Furtos, L. Versenyi, D. Prodan, R. Grecu, V. Simon, Journal of Optoelectronics and Advanced Materials, 7 (2005) 2849.

The invention claimed is:

1. An acrylic dental composite material comprising:
an organic compound which can be cured with light and which can be polymerized as the main matrix and, wherein the organic compound comprises BisGMA, HEMA, UDMA, and TEGDMA;
at least one of hydroxyapatite or β-tricalcium phosphate (β-TCP) for providing regenerative properties within the supportive phase,
at least one of CQ, diphenyl(2,4,6-trimethylbenzoyl) phosphine oxide, 1-phenyl-1,2-propandione and 4-EDMAB as a photo-initiator,
at least one of Al—Sr—OF and Al—Sr—Si—OF for providing antibacterial properties within a supportive phase comprising an oxyfluoride compound; and
at least one of $SiO_2$, $SiO_2$/Silane, Si/Zr nanocluster, Si/Zr/Silane nanocluster, $TiO_2$, $TiO_2$/Silane, $ZrO_2$, $ZrO_2$/Silane, 3YSZ for providing strength within the supportive phase system;
wherein the supportive phase provides regenerative and antibacterial characteristics to said composite material.

2. The acrylic dental composite material according to claim 1, wherein the organic compound comprises BisGMA between 1% and 5% by weight, HEMA between 5% and 10% by weight, UDMA between 5% and 10% by weight and TEGDMA between 1% and 5% by weight.

3. The acrylic dental composite material according to claim 1, wherein the acrylic dental composite material comprises CQ between 0.1 and 0.5 wt. %, diphenyl(2,4,6-trimethylbenzoyl)phosphine oxide between 0.1 and 0.5 wt. %, 1-phenyl-1,2-propandione between 0.1 and 0.5 wt. %, and 4-EDMAB between 0.5 and 1.0 wt. %.

4. The acrylic dental composite material according to claim 1, wherein the oxyfluoride compound is provided at a value between 1 and 40 wt. %.

5. The acrylic dental composite material according to claim 1, wherein the supportive phase is provided at a value between 1 and 90 wt. %.

6. The acrylic dental composite material according to claim 1, further comprising a pigment.

7. The acrylic dental composite material according to claim 6, wherein said pigment is selected from Duranat Yellow Iron Oxide (Pigment Yellow 42 & 43 CI 77492), Duranat Red Iron Oxide (Pigment Red 101 CI77491), Phenyl-bis (2,4,6-trimethylbenzoyl) phosphine-oxide, 1-Phenyl-1,2-propanedione, Diphenyl (2,4,6-trimethylbenzoyl)

phosphine-oxide, Duranat Brown Iron Oxide (Pigment Brown), Duranat Black Iron Oxide (Pigment Black 11 CI 77499), iron oxide ($Fe_2O_3$-10 red), ferric hydroxide (FeOOH-yellow), $TiO_2$, E171 Titanium Dioxide, Pigment White 6 CI77891, and any combination thereof.

8. The acrylic dental composite material according to claim 6-7, wherein an amount of pigment in the composite material is in range from 0.01 and 1 wt. %.

\* \* \* \* \*